United States Patent [19]

Schumann

[11] Patent Number: Plant 7,499

[45] Date of Patent: Apr. 16, 1991

[54] GERANIUM PLANT NAMED FISPOL

[75] Inventor: Ingeborg Schumann, Hoehr-Grenzhausen, Fed. Rep. of Germany

[73] Assignee: Florfis AG, Binningen, Switzerland

[21] Appl. No.: 426,564

[22] Filed: Oct. 25, 1989

[51] Int. Cl.[5] ..... A01H 5/00

[52] U.S. Cl. ..... Plt./68

[58] Field of Search ..... Plt./68

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A new and distinct cultivar of geranium plant named Fispol, particularly characterized by the combined features of carmine red semi-double flowers, medium green foliage, compact habit, early to medium flower response, and very good resistance to rain.

1 Drawing Sheet

The present invention comprises a new and distinct cultivar of geranium, botanically known as *Pelargonium zonale,* and hereinafter referred to by the cultivar name Fispol.

Fispol is a product of a planned breeding program which had the objective of creating new geranium cultivars with carmine red semi-double flower type, good chlorophyll quality, and better transportability.

Fispol was originated from a hybridization made by the inventor in a controlled breeding program in Galdar, Gran Cararia, Spain, in 1983. The female parent was Purpurball, characterized by its dark rose semi-double flowers and large umbels with long peduncles. The male parent of Fispol was a hybrid of Perlpenei, characterized by its white flowers and light green leaves, and pelfi® Bern, which has single orange-red flowers and dark green-brown foliage.

Fispol was discovered and selected as one flowering plant within the progeny of the stated cross by Ingeborg Schumann in May 1984 in a controlled environment in Hillscheid, Federal Republic of Germany.

The first act of asexual reproduction of Fispol was accomplished when vegetative cuttings were taken from the initial selection in February 1985 in a controlled environment in Hillscheid, Federal Republic of Germany by, or under the supervision of, Ingeborg Schumann.

Horticultural examination of selected units initiated in Spring 1984 and continuing thereafter has demonstrated that the combination of characteristics as herein disclosed for Fispol are firmly fixed and are retained through successive generations of asexual reproduction.

Fispol has not been observed under all possible environmental conditions. The phenotype may vary significantly with variations in environment such as temperature, light intensity and daylength.

The following observations, measurements and comparisons describe plants grown in Hillscheid, Federal Republic of Germany, under greenhouse conditions which approximate those generally used in commercial practice.

The following traits have been repeatedly observed and are determined to be basic characteristics of Fispol, which, in combination, distinguish this geranium as a new and distinct cultivar:

1. Light carmine red flowers.
2. Semi-double flower form.
3. Very good color in cloudy conditions.

4. Very good rain resistance.
5. Medium green foliage.
6. Compact to medium habit.
7. Ships well.

Of the many pelargonium cultivars known to the present inventor, the most similar in comparison to Fispol is the cultivar Polka, disclosed in U.S. Plant Pat. No. 5,371. Reference is made to attached Chart A which compares certain characteristics of fispol to those same characteristics of Polka. In general comparison to Polka, Fispol has a much better resistance to rain, and its flowers are a carmine or rose red, as opposed to the more reddish flower color of Polka.

The accompanying color photographic drawing shows typical flower and foliage characteristics of Fispol, with the colors being as true as possible with illutsrations of this type.

In the following description color references are made to The Royal Horticulatural Society Colour Chart. The color values were determined between 2:00 p.m. and 3:00 p.m. indoors on May 6, 1987 and outdoors on July 9, 1987 under 50,000 Lux light intensity at Hillscheid, Federal Republic of Germany.

Classification:

*Botanical.*—A hybrid of the genus *Pelargonium zonale* l'hert. cv Fispol.

*Commercial.*—Zonal geranium.

INFLORESCENCE

A. Umbel:

*Average diameter.*—Indoor, 9.8 cm; outdoor, 9.1 cm.

*Average depth.*—Indoor, 5.0 cm; outdoor, 4.7 cm.

*Peduncle length.*—Indoor, 16.1 cm; outdoor, 15.0 cm.

*Pedicel length.*—Indoor, 2.8 cm; outdoor, 2.3 cm.

B. Corolla:

*Average diameter.*—Indoor, 4.4 cm; outdoor, 4.4 cm.

*Form.*—Semi-double.

*Color (general tonality from a distance of three meters).*—Carmine red, 52A-B.

*Color (entire upper surface).*—RHS 52A.

*Color (lower surface).*—RHS 52A.

*Sepals.*—Green with weak red spots at the base.

*Pedicels.*—Upper third red with anthocyan.

C. Bud:

*Shape.*—Elliptic, almost round.

*Color.*—Light green.

D. Reproductive organs:

*Androecium.*—8–9 stamens.

*Gynoecium.*—5 lobed stigma.

E. Spring flowering response period: In Hillscheid, Federal Republic of Germany in 1988, 40% of plants with at least 1 flower opened 12 weeks after planting of unrooted cuttings.

F. Outdoor flower production: The flower count in 1988 in Hillscheid, Federal Republic of Germany indicated between 45 and 50 flowers per plant for June through October observation period.

G. Durability: Very good rain resistance.

PLANT:

A. Foliage:

*Form.*—Kidney shaped.

*Margin.*—Bicrenate.

*Color.*—Medium to dark green.

*Zonation.*—None.

*Tolerance to botrytis.*—Very good.

B. General appearance and form:

*Internode length.*—Compact to medium.

*Branching pattern.*—5.1 branches per plant after 13 weeks of growing time from unrooted cuttings.

*Height.*—23 cm on average.

CHART A

COMPARISON OF FISPOL AND POLKA

| | FISPOL | POLKA |
|---|---|---|
| Flower color | RHS 52A | RHS 46C |
| Zonation | Absent | Weak to medium |
| Flower size | 47–50 mm | 44–47 mm |
| Rain resistance | Very good | Good |

I claim:

1. A new and distinct cultivar of geranium plant named Fispol, as illustrated and described.

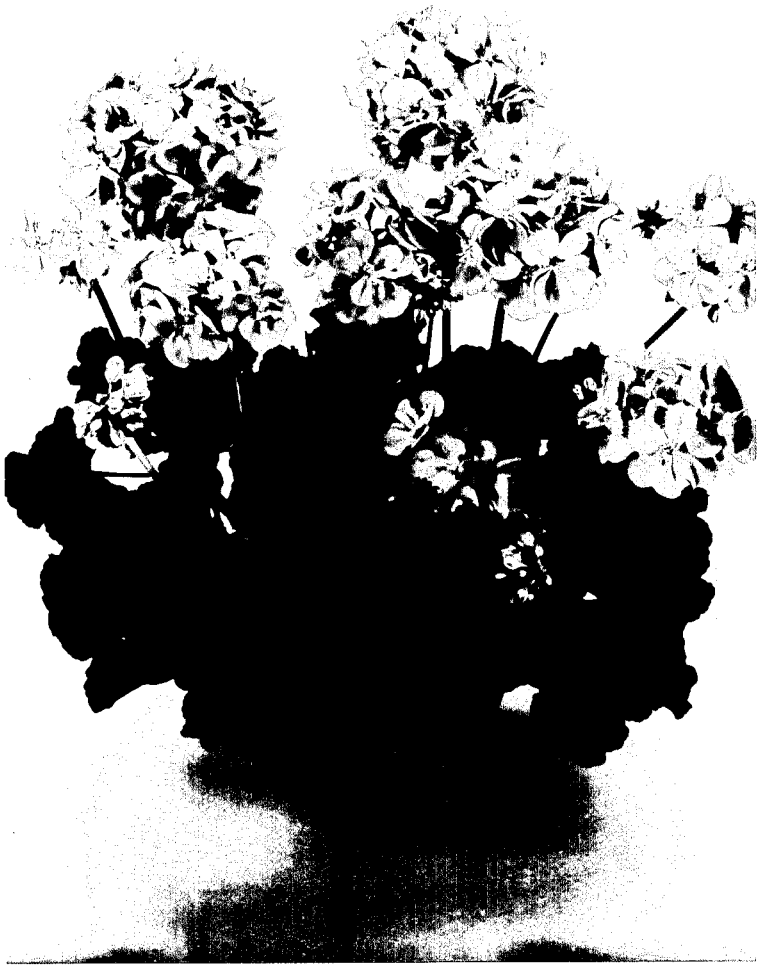

* * * * *